United States Patent [19]

Wong

[11] Patent Number: 5,063,026

[45] Date of Patent: Nov. 5, 1991

[54] EGG COLLECTING APPARATUS

[75] Inventor: Johnson N. S. Wong, Rolling Hills, Calif.

[73] Assignee: Evergreen Industries, Inc., Los Angeles, Calif.

[21] Appl. No.: 552,199

[22] Filed: Jul. 11, 1990

[51] Int. Cl.⁵ .................. C12M 1/28; A61B 10/00
[52] U.S. Cl. ..................... 422/102; 422/99; 128/749; 128/759; 435/30; 435/292; 435/294
[58] Field of Search .......... 422/99, 101, 102; 128/749, 759; 435/294, 296, 292, 30

[56] References Cited

U.S. PATENT DOCUMENTS

| | | | |
|---|---|---|---|
| 2,969,057 | 1/1961 | Simmons | 128/759 |
| 3,661,718 | 5/1972 | Sterling | 435/30 |
| 3,846,248 | 1/1970 | Rose | 435/30 |
| 4,150,950 | 4/1979 | Takeguchi et al. | 128/759 |
| 4,237,223 | 12/1980 | Metz | 435/30 |
| 4,368,272 | 1/1983 | Kashket | 435/30 |

Primary Examiner—Robert J. Warden
Assistant Examiner—Howard Hampel
Attorney, Agent, or Firm—Nilsson, Robbins, Dalgarn, Berliner, Carson & Wurst

[57] ABSTRACT

A collecting apparatus for the collection of pinworm eggs incorporates a shaft surrounded by an adhesive strip. A tab is disposed at the free end of the adhesive strip. The shaft is attached to a gripping member by a connecting member.

The gripping member is preferably a threaded screw cap suitable for use with a storage tube. The shaft and connecting member are placed within the tube and the tube is sealed with the gripping member for transportation and storage of collected eggs. Once a specimen is collected, the tab of the adhesive strip is used as an anchor. Using the gripping member as a tool in a rotating fashion, the entire adhesive strip is rolled onto a microscope slide without disturbing any specimens on the strip.

8 Claims, 1 Drawing Sheet

EGG COLLECTING APPARATUS

BACKGROUND OF THE INVENTION

Pinworm infections are familiar to parents of young children worldwide. Enterobius vermicularis, commonly known as the pinworm, is parasitic only to humans. Mature worms inhabit the human intestinal tract. However, the female worm ordinarily deposits her eggs in the perianal region and diagnosis of a pinworm infection is usually based on the recovery of the pinworm eggs from this region.

Two types of procedures are commonly used to diagnose pinworm infections. The most reliable diagnostic procedure for finding eggs is to press a strip of cellulose tape on the perianal skin, remove it, and place the tape on a clean microscope slide for examination. The application of adhesive cellulose tape to the perianal region first thing in the morning will usually demonstrate infection.

The second type of diagnostic procedure is the vaseline-paraffin swab. This requires a cotton swab to be dipped in a mixture of vaseline and parawax to thoroughly coat the swab. Such swabs may be stored for long periods if the storage temperature is not such that the vaseline-paraffin on the swab melts. At least four consecutive negative swabs should be obtained before the patient is considered free of infection.

Most laboratories use the cellulose tape method. Generally, the cellulose tape procedure uses a strip of clear cellulose tape, ¾ inch wide. A piece of tape about four to five inches long is anchored on the underside of a three by one inch slide and smoothed across the top of the slide. A paper label or tab is affixed to the free end of the tape for labeling and identification, and to provide a grip for manipulating the tape.

To collect a sample of pinworm eggs from the perianal area, a wooden tongue depressor or a test tube is held as a support against the back of a slide with cellulose tape affixed to the front of the slide, as described above. The cellulose tape is pulled back from the slide by gripping the label and looping the tape, adhesive side outward, over the support. Pinworm eggs are collected as the sticky tape surface is pressed against the perianal skin.

Once the eggs are collected, the tape is smoothed back into place over the slide, adhesive side down. The patient's name and the date are placed on the label.

Examination of the slide is performed under the low power of a microscope. To make the eggs more visible, the label is gripped and the tape lifted from the slide. A drop of toluene or xylene is placed on the slide, then the tape is smoothed back into position. The toluene or xylene serves to clear the preparation; and under low light intensity, the eggs stand out prominently.

The cellulose tape diagnostic method of the prior art is awkward because it requires the collector to loop the cellulose tape, adhesive side up, over a tongue depressor or test tube. Further, the collector's hands must be adjacent to the perianal area in order to effectively collect eggs while retaining the tape in a fixed position over the support. Thus, the collector exposes his or her hands to infection while collecting the eggs and when the tape is replaced over the slide.

SUMMARY OF THE INVENTION

In general, the present invention comprises an apparatus for the collection of nematode or pinworm eggs. The collecting apparatus includes a shaft having an exterior surface, a gripping member and a connecting member for attaching the shaft to the gripping member. An adhesive strip with a tab attached to one end is disposed to surround the exterior surface of the shaft.

In the disclosed embodiment, the adhesive strip surrounds the exterior surface of the shaft with the adhesive side outward and with the tab positioned at its free end so that the tab may be used to remove the strip from the shaft for transference of the tape to a microscope slide for examination. In an alternative embodiment, a storage tube is adapted to contain the shaft and the connecting member within its interior. The tube includes an open threaded end and the gripping member is threaded for interlocking engagement with the tube when the shaft and connecting member are positioned within the interior of the tube.

The present invention decreases the risk of exposure to infection inherent in the cellulose tape diagnostic method of the prior art by placing the collector's hands on the gripping member a substantial distance from the cellulose tape on the shaft, determined by the length of the connecting member. The longer the connecting member, the greater the distance of the collector's hands from the perianal area when egg collection is performed.

Additionally, prior to egg collection, the shaft and connecting member may be stored within the interior of the tube. The adhesive tape is prepositioned on the shaft such that the adhesive side is outward. As a result, when egg collection begins, there is no need to fold back the adhesive strip, as required in the diagnostic method of the prior art. Indeed, there is no reason for the collector to touch the adhesive strip or the tab because after collection of the eggs, the shaft and the connecting member may be reinserted into the tube for safe and secure transportation to a laboratory.

BRIEF DESCRIPTION OF THE DRAWINGS

In the drawings, which constitute a part of this specification, an exemplary embodiment exhibiting various objectives and features hereof is set forth, specifically.

DESCRIPTION OF THE ILLUSTRATIVE EMBODIMENT

As required, a detailed illustrative embodiment of the present invention is disclosed herein. However, it is merely representative recognizing that various mechanical components and various structural elements may be embodied in a wide variety of forms, some of which may be quite different from those specific structural and functional details disclosed herein. Consequently, the details disclosed herein are merely representative; yet in that regard they are deemed to afford the best embodiment for the purposes of disclosure to provide a basis for claims herein which define the scope of the present invention.

Figure 1:
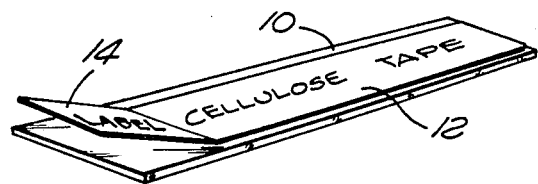
FIG. 1 is a plan view of the apparatus of the prior art prior to use.
Figure 2:
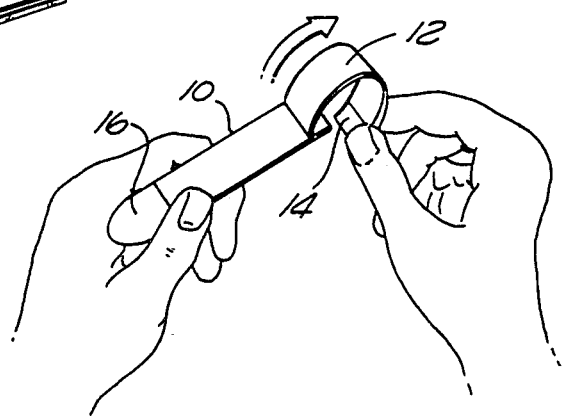
FIG. 2 is a perspective view illustrating a collector practicing the prior art cellulose tape diagnostic method.

Referring initially to FIGS. 1 and 2, a cellulose tape diagnostic method of the prior art is illustrated. In FIG. 1, a microscope slide 10 is shown with a strip of clear cellulose tape 12 anchored to the top of the slide, adhesive side down. A paper tab or label 14 is affixed to the free end of the tape for labeling and removal of the tape 12 from the slide 10.

Using this prior art method, prior to the collection of eggs, the collector must expose the adhesive side of the tape 12. As shown in FIG. 2, a test tube or a wooden tongue depressor 16 is placed against the underside of the slide 10 to provide support and to extend the length of the slide. The collector then exposes the adhesive side of the tape 12 from the slide 10 by gripping the label 14 and looping the tape 12, adhesive side outward, over the remote end of the tongue depressor 16. To collect pinworm eggs, the collector holds the tape 12 firmly in place against the back of the tongue depressor 16 while pressing the adhesive side of the tape 12 firmly against the perianal folds.

After a specimen has been collected, the collector spreads the tape 12 back over the slide 10, adhesive side down. The patient's name and the date is placed on the label or onto the labelling area of the slide. The slide and sample are then transported to a laboratory for examination.

Figure 3:
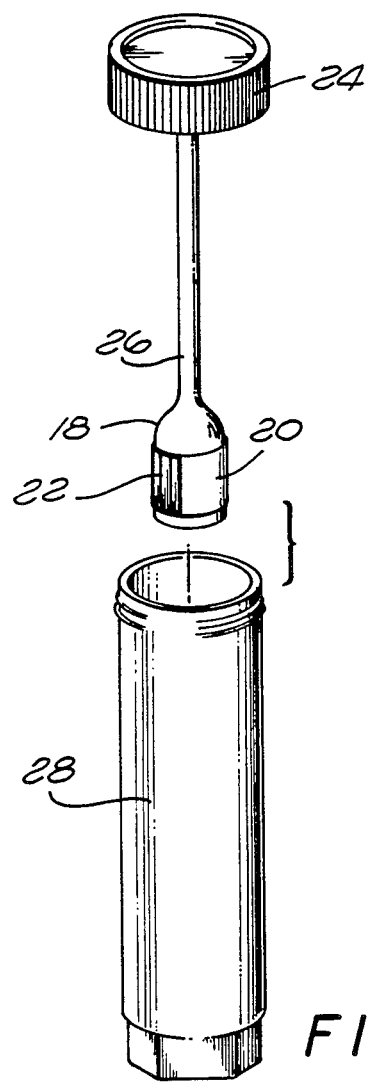
FIG. 3 is a perspective view of the egg collecting apparatus in accordance with the present invention.

The present invention comprises an apparatus which requires no preparation or exposure of the adhesive strip prior to use. As shown in FIG. 3, a shaft 18 is surrounded on its exterior surface by a strip of adhesive tape 20, adhesive side out. A paper tab 22 is attached to the free end of the tape 20 to provide a handle for gripping the tape.

In the preferred embodiment, the shaft is a cylinder end made of polypropylene or other plastic material. However, shafts of varying sizes and shapes may be effectively incorporated in the present invention.

The collector holds the collecting apparatus with a gripping member 24. A connecting member 26 attaches the shaft 18 to the gripping member 24. With the collector's hand holding the gripping member 24 and applying gentle pressure, the shaft 18 and the tape 20 are pressed against the perianal folds during egg collection.

In the preferred embodiment, the connecting member 26 is an extension of the lower end of the shaft 18. The connecting member is then inserted into a receptacle in the gripping member 24. The connecting member 26 is also preferably made of polypropylene.

In an alternative embodiment, a test tube 28 is incorporated in the present invention to provide a means for storage and transportation. The tube 28 is preferably made of polypropylene or other suitable plastic material. The top of the tube 28 is threaded for interlocking engagement with the gripping member 24. Consequently, the gripping member 24 is preferably a high density polyethylene screw cap capable of providing a reliable leak-proof seal with the tube 28.

Prior to egg collection, the tube 28 is sealed by the interlocking engagement between its open end and the gripping member 24. The shaft 18, with the adhesive tape 20 surrounding its exterior surface, and the connecting member 26 are stored within the interior of the tube 28. In this way, the adhesive side of the tape 20 is protected from airborne contaminants.

In the preferred embodiment of the tube, shaft and connecting member, the diameter of the tube 28 is approximately two and one-half (2½) times larger than the diameter of the shaft 18. The diameter of the connecting member is less than the diameter of the shaft. The differential between the diameters allows the shaft 18, adhesive tap 20, tab 22 and connecting member 26 to be removed from and inserted into the tube 28 without touching the tape 20 to the sides of the tube 28.

Prior to use, the collector grasps the gripping member 24 and unscrews the gripping member 24 from the tube 28. Next, while holding the gripping member 24, the collector removes the shaft 18 and the connecting member 26 from the tube 28. The collector then presses the adhesive tape 20, surrounding the shaft 18, to the perianal areas of the infected patient, rotating the shaft 18 from side to side. Once a specimen is collected, the collector reinserts the shaft 18 and the connecting member 26 into the tube 28 and screws the gripping member 24 back onto the top of the tube 28.

The collected specimen, sealed within the tube 28, then may be transported to a laboratory for examination in a safe manner. Prior to examination, the shaft 18 and the connecting member 26 are removed from the interior of the tube 28 from the tube 28 by unscrewing the gripping member 24.

Figure 4:
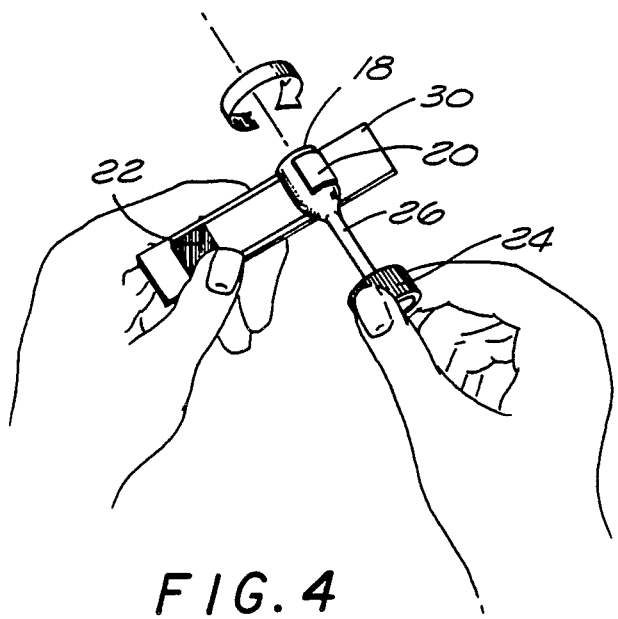
FIG. 4 is a perspective view of the egg collecting apparatus as the cellulose tape is transferred to a microscope slide.

Next, as shown in FIG. 4, the examining technician unrolls the tape 20 from the shaft 18 by holding or anchoring the tab 22 on the end of a microscope slide 30. The technician then rotates the gripping member 24 to roll the shaft 18 along the top of the slide 30. As the shaft 18 is rolled, the adhesive side of the tape 20 adheres to the slide 30. The gripping member 24 is rotated until the tape 20 is fully extended along the length of the slide 30.

The slide 30 may then be examined under the low power of a microscope. To make the eggs more visible, the tape 20 is lifted from the slide 30 by gripping the tab 22 and pulling it upwards. The technician then adds a dorp of toluene or xylene to the slide and presses the tape 20 down on the slide 30 again.

In view of the above description of the preferred embodiment, it will be apparent that the present invention is capable of economic implementation in a variety of shapes and functional designs to accomplish an effective, economical and easy-to-use safe collection apparatus. Such modifications may include varying the shape and size of the shaft, gripping member and/or connecting member. Various types of adhesive materials may be used in place of the cellulose tape. Additionally, any material which can be effectively attached to an adhesive material and used for labeling and gripping may be used as the label. The tube may take any shape or form sufficient to thold the shaft and connecting member within its interior. Consequently, the scope of the present invention hereof is deemed to be appropriately determined by the claims as set forth below.

I claim:

1. An apparatus for the collection of parasitic eggs, comprising:
    an adhesive strip having a first end, a second end, an adhesive side and a non-adhesive side;
    a tab attached to the first end of the strip;
    a shaft having an exterior surface adapted for receipt of the non-adhesive side of the strip;
    the adhesive strip being removably wrapped around the exterior surface of the shaft with the adhesive side of the strip exposed and the tab overlapping the second end of the strip;
    a gripping member; and
    a connecting member having two ends, the connecting member being attached at one end to the shaft and connected at the other end to the gripping member.

2. The apparatus of claim 1 wherein:
the shaft is a cylinder.

3. The apparatus of claim 1 wherien:
the shaft is a hollow, three dimensional geometric figure.

4. The apparatus of claim 1 wherien
the adhesive strip is cellulose tape.

5. The apparatus of claim 1 further comprising
a tube adapted to contain the shaft and the connecting member within the interior of the tube.

6. The apparatus of claim 5 wherien:
the tube includes an open end; and
the gripping member is adapted for interlocking engagement with the open end of the tube.

7. The apparatus of claim 6 wherein:
the open end of the tube is threaded; and the gripping member is a threaded screw cap.

8. An apparatus for the collection of parasite eggs, comprising:
an adhesive strip having a first end, an adhesive side and a non-adhesive side;
a tab attached to the first end of the strip;
a cylinder having an exterior surface and having a diameter that is substantially uniform over a sufficient length to facilitate wrapping of the non-adhesive side of the strip around the exterior surface of the cylinder;
the adhesive strip being removably wrapped around the exterior surface of the cylinder with the adhesive side of the strip exposed and the tab overlapping the second end of the strip;
a gripping member;
a connecting member having two ends, the connecting member being connected at one end to cylinder and connected at the other end to the gripping member; and
a tube adapted to contain the cylinder and the connecting member within the interior of the tube.

* * * * *